(12) United States Patent
Chang et al.

(10) Patent No.: US 7,941,278 B2
(45) Date of Patent: May 10, 2011

(54) MICRORNA MOTIFS

(75) Inventors: Yu-Ching Chang, Hsinchu County (TW); Yu-Yu Lin, Yilan County (TW); Shiu-Chieh Lan, Taichung (TW); Cheng-Tao Wu, Taipei County (TW); Chung-Cheng Liu, Hsinchu (TW)

(73) Assignee: Industrial Technology Research Institute, Hsinchu (TW)

( * ) Notice: Subject to any disclaimer, the term of this patent is extended or adjusted under 35 U.S.C. 154(b) by 1102 days.

(21) Appl. No.: 11/617,038

(22) Filed: Dec. 28, 2006

(65) Prior Publication Data

US 2007/0275392 A1    Nov. 29, 2007

Related U.S. Application Data

(60) Provisional application No. 60/755,427, filed on Dec. 30, 2005.

(51) Int. Cl.
*G06F 7/00* (2006.01)

(52) U.S. Cl. ............... 702/19; 702/20; 703/11; 707/700; 536/23.1

(58) Field of Classification Search .................. None
See application file for complete search history.

(56) References Cited

U.S. PATENT DOCUMENTS

| 2005/0075492 A1 | 4/2005 | Chen |
| 2005/0142581 A1 | 6/2005 | Griffey |
| 2005/0266552 A1 | 12/2005 | Doench |
| 2005/0272923 A1 | 12/2005 | Zhang |
| 2007/0042380 A1 | 2/2007 | Bentwich |

FOREIGN PATENT DOCUMENTS

| WO | WO2004/048511 | 6/2004 |
| WO | WO2004/066183 | 8/2004 |
| WO | WO2005/111211 | 11/2005 |

OTHER PUBLICATIONS

Xie et al. 2005 Nature vol. 434 pp. 338-345.*
Altschul SF, Gish W, Miller W, Myers EW, Lipman DJ J, "Basic Local Alignment Search Tool," Mol Biol. Oct. 5, 1990; 215(3):403-410.
Berezikov E, Guryev V, van de Belt J, Wienholds E, Plasterk RH, Cuppen E, "Phylogenetic Shadowing and Computational Identification of Human microRNA Genes," Cell. Jan. 14, 2005; 120(1):21-24.
Chang YC, Lan SJ, Lin YY, Wu CT, "Explore MicroRNA Precursors through a High-Throughput Computational Prediction," The Seventeenth International Conference on Genome Informatics, Poster and Software Demonstrations, P106-1 ~ P106-2, Yokohama, Japan, Dec. 2006.
Grad Y, Aach J, Hayes GD, Reinhart BJ, Church GM, Ruvkun G, Kim, "Computational and Experimental Identification of C. elegans microRNAs," J Mol Cell. May 2003; 11(5):1253-1263.
Kim VN, "MicroRNA Biogenesis : Coordinated Cropping and Dicing," Nat Rev Mol Cell Biol. May 2005; 6(5):376-385.
Lagos-Quintana M, Rauhut R, Lendeckel W, Tuschl T, Identification of Novel Genes Coding for Small Expressed RNAs, Science. Oct. 26, 2001; 294(5543):853-858.
Lagos-Quintana M, Rauhut R, Meyer J, Borkhardt A, Tuschl T, New microRNAs from mouse and human, RNA. Feb. 2003;9(2):175-9.
Lagos-Quintana M, Rauhut R, Yalcin A, Meyer J, Lendeckel W, Tuschl T, Identification of Tissue-Specific MicroRNAs from Mouse, Curr Biol. Apr. 30, 2002; 12(9):735-739.
Lau NC, Lim LP, Weinstein EG, Bartel DP, "An Abundant Class of Tiny RNAs with Probable Regulatory Roles in Caenorhabditis elegans," Science. Oct. 26, 2001; 294(5543):858-862.
Lee RC, Ambros V, "An Extensive Class of Small RNAs in Caenorhabditis elegans," Science. Oct. 26, 2001; 294(5543):862-864.
Lim LP, Glasner ME, Yekta S, Burge CB, Bartel DP, "Vertebrate MicroRNA Genes," Science. Mar. 7, 2003;299(5612):1540.
Lim LP, Lau NC, Garrett-Engele P, Grimson A, Schelter JM, Castle J, Bartel DP, Linsley PS, Johnson JM., "Microarray analysis shows that some microRNAs downregulate large numbers of target mRNAs," Nature. Feb. 17, 2005; 433(7027):769-773.
Lim LP, Lau NC, Weinstein EG, Abdelhakim A, Yekta S, Rhoades MW, Burge CB, Bartel DP. "The microRNAs of Caenorhabditis elegans," Genes Dev. Apr. 15, 2003; 17(8):991-1008.
Nam JW, Shin KR, Han J, Lee Y, Kim VN, Zhang BT., Human microRNA prediction through a probabilistic co-learning model of sequence and structure, Nucleic Acids Res. Jun. 24, 2005; 33(11):3570-3581.
Wang X, Zhang J, Li F, Gu J, He T, Zhang X, Li Y, MicroRNA identification based on sequence and structure alignment, Bioinformatics. Sep. 15, 2005; 21(18):3610-3614.
Xie X, Lu J, Kulbokas EJ, Golub TR, Mootha V, Lindblad-Toh K, Lander ES, Kellis M, "Systematic discovery of regulatory motifs in human promoters and 3' UTRs by comparison of several mammals," Nature. Mar. 17, 2005; 434(7031):338-345.
Xue C, Li F, He T, Liu GP, Li Y, Zhang X, "Classification of real and pseudo microRNA precursors using local structure-sequence features and support vector machine," BMC Bioinformatics. Dec. 29, 2005; 6:310.
Yang LH, Hsu W, Lee ML, Wong L, "SVM-based identification of microRNA precursors," Proceedings of 4th Asia-Pacific Bioinformatics Conference, 267-276, Taipei, Taiwan, Feb. 2006.
Yu et al, "Feature Selection for High-Dimensional Data: A Fast Correlation-Based Filter Solution," Proceedings of the Twentieth International Conference on Machine Leaning (ICML-03) 2003, 856-863.

* cited by examiner

*Primary Examiner* — Mary K Zeman
(74) *Attorney, Agent, or Firm* — Finnegan, Henderson, Farabow, Garrett & Dunner

(57) ABSTRACT

Disclosed are methods of identifying microRNA motifs or microRNA precursors for a target gene or a set of target genes. Also disclosed are related computer-readable media.

12 Claims, 2 Drawing Sheets

US 7,941,278 B2

MICRORNA MOTIFS

RELATED APPLICATION

This application claims priority to U.S. application Ser. No. 60/755,427, filed Dec. 30, 2005, the contents of which are incorporated herein by reference.

BACKGROUND

MicroRNAs (miRNAs) are a group of endogenous ~21-23 nt noncoding RNAs. They regulate expression of genes at the posttranscriptional level (Bartel, 2004 Cell, 116(2):281-97). Although only recently discovered, they have been found to play key roles in a wide variety of biological processes, including cell fate specification, cell death, cell proliferation, and fat storage. So far, more than 300 different human miRNAs have been identified (Griffiths-Jones, 2004, Nucleic Acids Res. 32 D109-111). Most of them are thought to recognize their mRNA targets via partial antisense complementarity. This partial complementarity, as well as the short lengths of miRNAs and their targets, makes identification of novel miRNAs difficult by conventional sequence comparison methods. Thus, there is a need for a novel approach for identifying miRNAs and their targets.

SUMMARY

This invention is based on the development of a computational method for predicting miRNAs and their targets.

In one aspect, this invention features a method of identifying a microRNA motif for a set of target genes. The method includes (a) providing a set of subject nucleic acid sequences that contain coding regions (CDRs), 5' untranslated regions (5' UTRs), and 3' untranslated regions (3' UTRs) of the target genes; and (b) determining the $DIFF_{CDRs}$ or $DIFF_{5'UTRs}$ value of a test RNA motif in the subject nucleic acid sequences by a set of functions as follows:

$$DIFF_{CDRs} = f(OBS_{3'UTRs}, OBS_{CDRs}, EXP_{3'UTRs}, EXP_{CDRs}) \quad \text{(I) and}$$

$$DIFF_{5'UTRs} = g(OBS_{3'UTRs}, OBS_{5'UTRs}, EXP_{3'UTRs}, EXP_{5'UTRs}) \quad \text{(II).}$$

In the above functions, $DIFF_{CDRs}$ and $DIFF_{5'UTRs}$ represent the degrees of the enrichment of the test motif in all of the 3' untranslated regions in comparison with all of the coding regions and all of the 5' untranslated regions, respectively; $OBS_{3'UTRs}$, $OBS_{CDRs}$, and $OBS_{5'UTRs}$ represent the observed counts of the test motif within all of the 3' untranslated regions, all of the coding regions, and all of the 5' untranslated regions, respectively; and $EXP_{3'UTRs}$, $EXP_{CDRs}$, and $EXP_{5'UTRs}$ represent the expected counts of the test motif within all of the 3' untranslated regions, all of the coding region, and all of the 5' untranslated region, respectively. The two functions mentioned above can take the form of Formula III and IV below:

$$DIFF_{CDRs} = \frac{OBS_{3'UTRs} - OBS_{CDRs}}{MAX(EXP_{3'UTRs}, EXP_{CDRs})} \quad \text{and} \quad \text{(III)}$$

$$DIFF_{5'UTRs} = \frac{OBS_{3'UTRs} - OBS_{5'UTRs}}{MAX(EXP_{3'UTRs}, EXP_{5'UTRs})}. \quad \text{(IV)}$$

The test motif can be a contiguous RNA segment containing 5 to 11 nucleotides. The set of target genes can be expressed in a pre-determined biological sample, which can be prepared from a tissue (e.g., a brain tissue or a liver tissue) or a cell culture (e.g., a HepG2 cell culture). In one embodiment, the set of target genes is determined from the microarray expression profiles provided by the Genomics Institute of the Novartis Research Foundation.

The invention also features a method of identifying a microRNA motif for a target gene. The method includes (a) providing a subject nucleic acid sequence that contains coding regions (CDRs), 5' untranslated regions (5' UTRs), and 3' untranslated regions (3' UTRs) of the target gene; and (b) determining the $DIFF_{CDRs}$ or $DIFF_{5'UTRs}$ value of a test RNA motif in the subject nucleic acid sequences by a set of functions as follows:

$$DIFF_{CDRs} = f(OBS_{3'UTRs}, OBS_{CDRs}, EXP_{3'UTRs}, EXP_{CDRs}) \quad \text{(V) and}$$

$$DIFF_{5'UTRs} = g(OBS_{3'UTRs}, OBS_{5'UTRs}, EXP_{3'UTRs}, EXP_{5'UTRs}) \quad \text{(VI).}$$

$DIFF_{CDRs}$ and $DIFF_{5'UTRs}$ represent the degrees of the enrichment of the test motif in all of the 3' untranslated regions in comparison with all of the coding regions and all of the 5' untranslated regions, respectively; $OBS_{3'UTRs}$, $OBS_{CDRs}$, and $OBS_{5'UTRs}$ represent the observed counts of the test motif within all of the 3' untranslated regions, all of the coding regions, and all of the 5' untranslated regions, respectively; and $EXP_{3'UTRs}$, $EXP_{CDRs}$, and $EXP_{5'UTRs}$ represent the expected counts of the test motif within all of the 3' untranslated regions, all of the coding regions, and all of the 5' untranslated regions, respectively. The set of functions can take the form of Formula VII and VIII below:

$$DIFF_{CDRs} = \frac{OBS_{3'UTRs} - OBS_{CDRs}}{MAX(EXP_{3'UTRs}, EXP_{CDRs})} \quad \text{and} \quad \text{(VII)}$$

$$DIFF_{5'UTRs} = \frac{OBS_{3'UTRs} - OBS_{5'UTRs}}{MAX(EXP_{3'UTRs}, EXP_{5'UTRs})}. \quad \text{(VIII)}$$

The test motif can be a contiguous segment containing 5 to 11 nucleotides.

In another aspect, the invention features a method for identifying a microRNA precursor. The method includes:

(a) providing a subject DNA sequence;

(b) searching, by a heuristic algorithm, in the subject DNA sequence of step (a) for a DNA region that has a strong tendency to form a stem loop;

(c) retaining a DNA region of step (b) that does not reside in a low complexity region of the subject DNA sequence;

(d) accessing the ability of the retained DNA region of step (c) to fold into a secondary structure, and selecting a DNA region whose corresponding RNA sequence has a low energy of folding and forms a stem loop;

(e) comparing the energy of folding of two selected DNA regions of step (d) that overlap with each other substantially such that both overlap ratios exceed a predetermined value, and choosing the one with the lowest energy of folding;

(f) assessing the stability of a chosen DNA region of step (e) by performing randomized shuffle of the chosen DNA region a number of times, while keeping a characteristic property of the chosen DNA region unchanged, and calculating a score as a measure of the stability of the secondary structure formed by the chosen DNA region; and (g) identifying, from one or more chosen DNA regions, a target section that has a stability score higher than a predetermined value. The target section is determined to be a microRNA precursor. The subject DNA sequence can contain a genomic DNA sequence, such as genomic DNA sequence from a metazoan species (e.g., *Homo Sapiens*).

The low complexity region in step (c) can be a region of biased composition including homo-polymeric runs, short-period repeats, or subtler overrepresentation of one or more nucleotides. Various web-based sequence alignment servers (such as BLAST server) can be used for filtering the results against such regions since they tend to generate spurious results that reflect compositional bias rather than significant alignments. Genomic DNA sequences with low complexity regions masked out by tools such as RepeatMasker (http://www.repeatmasker.org) or Tandem Repeat Finder (G. Benson, Nucleic Acids Res., 1999, 27, 573-580) are available for download. The energy of folding in step (d) can be calculated with an RNA secondary structure prediction tool, e.g., Vienna RNA package (Hofacker et al., 1994, Monatsh. Chem., 125, 167-188). Preferably, the low energy of folding in step (d) is no greater than −18 kcal/mol, e.g., no greater than −20 kcal/mol, −21 kcal/mol, −22 kcal/mol, −23 kcal/mol, −24 kcal/mol, or −25 kcal/mol. The phrase "overlap with each other substantially" refers to that the overlap ratio of the two DNA regions exceeds a pre-determined value. For example, an overlap ratio of two regions $R_A=[nt100, nt200]$ and region $R_B=[nt110, nt220]$ can be calculated as 90% according to the formula $$\frac{\text{overlaping\_length}}{\min(RA\_length, RB\_length)} = \frac{90}{\min(100, 110)} = 90\%.$$

The characteristic property of the DNA region in step (f) can be a mono-nucleotide distribution or a di-nucleotide distribution.

The above-mentioned heuristic algorithm can further include (1) selecting a pair of seeds (i.e., two contiguous segments, each having a length of 3 to 8 nucleotides) that are spaced within a pre-determined distance, wherein the bases of the seeds match to each other according to a base pairing rule (e.g., matching Watson-Crick complementary base pairs (A-T, T-A, C-G, and G-C) or matching non-canonical G-T wobble base pairs (G-T and T-G)); and (2) extending, from the pair of seeds, the DNA region in the direction toward and away from each other using an extension rule, and stopping the extension upon the fulfillment of a criterion. The extension in step (2) can include extending in the respective direction when the sequence identity ratio is higher than a pre-determined value; matching base pairs according to the base paring rule; and adding short gaps as necessary to improve the sequence identity ratio and allow for deletion and insertion of nucleotides. The criterion can include stopping the extension when there is no way of satisfying the rule or when the region is longer than a pre-determined length.

In a further aspect, the invention features a method for identifying a microRNA precursor related to a specific biological sample. The method includes (a) taking as input the test value $\text{DIFF}_{CDRs}$ and $\text{DIFF}_{5'UTRs}$ determined by the method and target sections identified by the methods described above, and generating a set of features from said test motifs and values and a characteristic property of said target sections; (b) selecting a set of significant features from said set of features by a procedure based on information theory; (c) applying a machine learning procedure to facilitate the classification of the test motifs and the microRNA precursors; (d) comparing the target section to a microRNA motif for a set of target genes identified by a method described herein; and (e) determining whether the target section includes a fragment that is identical or complementary to the microRNA motif. The target section is determined to be a specific microRNA precursor if the target section contains a segment that is identical or complementary to the microRNA motif; and the target section is determined to be a non-specific microRNA precursor if the target section contains no segment that is identical or complementary to the microRNA motif. The characteristic property of the target section can be a sequence-based property, a structure-based property, or a domain knowledge-based property. The selecting step can include employing a correlation-based filtering technique. The machine learning procedure can include employing a probabilistic classifier technique, a support vector machine (SVM) technique, a decision tree technique, or a neural network technique. The test motif identified in step (c) contains information specific to a biological sample.

In another aspect, the invention features a computer readable medium including software for effecting the following steps: receiving a set of subject nucleic acid sequences, determining a $\text{DIFF}_{CDRs}$ or $\text{DIFF}_{5'UTRs}$ value for at least one RNA motif in the subject nucleic acid sequences according to a method described herein, and outputting the $\text{DIFF}_{CDRs}$ or $\text{DIFF}_{5'UTRs}$ value.

In a further aspect, the invention features a computer readable medium including software for effecting the following steps receiving a subject DNA sequence, identifying a microRNA precursor based on the subject DNA sequence according to the method described above, and outputting the sequence of the microRNA precursor. The software can further effect comparing the sequence of the microRNA precursor to a microRNA motif for a set of target genes identified by a method described above to identify a segment that is identical or complementary to the microRNA motif. The set of target genes can be expressed in a pre-determined biologic sample, which can be prepared from a tissue (e.g., a brain tissue or a liver tissue) or a cell culture (e.g., a HepG2 cell culture). The software can further effect outputting the sequence of the microRNA precursor that has a segment identical or complementary to the microRNA motif or that has no segment identical or complementary to the microRNA motif.

In yet another example, the invention features a computer-readable medium on which is stored a database capable of configuring a computer to respond to queries based on a record belonging to the database. The record includes a first value that identifies a target gene and a second value that identifies a specific microRNA motif or non-specific microRNA motif associated with the target gene. The specific microRNA motif or non-specific microRNA motif is obtained by the method described above. The record can include a third value that identifies tissue specificity data associated with the target gene. In one example, the record includes the sequence of each microRNA motifs listed in Table 1 below. The set of target genes can be expressed in a pre-determined biologic sample, which can be prepared from a tissue (e.g., a brain tissue or a liver tissue) or a cell culture (e.g., a HepG2 cell culture). In one embodiment, the set of target genes is determined from the microarray expression profiles provided by the Genomics Institute of the Novartis Research Foundation.

The term "target gene" refers to a gene intended for down-regulation via RNA interference ("RNAi"). The term "RNA interference" or "RNAi" refers generally to a sequence-specific or selective process by which a target molecule (e.g., a target gene, protein or RNA) is downregulated. Within the scope of this invention is utilization of RNAi featuring degradation of RNA molecules (e.g., within a cell). Degradation is catalyzed by an enzymatic, RNA-induced silencing complex (RISC). RNAi occurs in cells naturally to remove foreign RNAs (e.g., viral RNAs). Natural RNAi proceeds via fragments cleaved from free double-stranded RNA, which directs the degradative mechanism. Alternatively, RNAi can be initiated by the hand of man, for example, to silence the expression of target genes.

The term "target protein" refers to a protein intended for downregulation via RNAi. The term "target RNA" refers to a RNA sequence that is recognized by a microRNA via partial antisense complementarity. Examples of a target RNA include, but not limited to, sequences known or believed to be involved in the etiology of a given disease, condition or pathophysiological state, or in the regulation of physiological function. A target RNA may be derived from any living organism, such as a vertebrate, particularly a mammal and more particularly a human, or from a virus, bacterium, fungus, protozoan, parasite or bacteriophage. A target RNA may comprise wild type sequences, or, alternatively, mutant or variant sequences, including those with altered stability, activity, or other variant properties, or hybrid sequences to which heterologous sequences have been added. Furthermore, a target RNA can include a RNA sequence that has been chemically modified, such as, for example, by conjugation of biotin, peptides, fluorescent molecules, and the like.

As used herein, the term "microRNA" refers to any type of interfering RNAs, including but not limited to, endogenous microRNAs and artificial microRNAs. Endogenous microRNAs are small RNAs naturally present in the genome which are capable of modulating the productive utilization of mRNA. An artificial microRNA can be any type of RNA sequence, other than endogenous microRNA, which is capable of modulating the productive utilization of mRNA. For instance, it includes sequences previously identified as siRNA, regardless of the mechanism of down-stream processing of the RNA. A microRNA sequence can be an RNA molecule composed of any one or more of these sequences. MicroRNA sequences have been described in publications such as, Lim, et al., 2003, Genes & Development, 17, 991~1008, Lim et al., 2003, Science, 299, 1540, Lee and Ambrose, 2001, Science, 294, 862, Lau et al., 2001, Science 294, 858-861, Lagos-Quintana et al., 2002, Current Biology, 12, 735-739, Lagos-Quintana et al., 2001, Science, 294, 853~857, and Lagos-Quintana et al., 2003, RNA, 9, 175-179, which are incorporated herein by reference. Examples of microRNAs include any RNA that is a fragment of a larger RNA or is a miRNA, siRNA, stRNA, sncRNA, tncRNA, snoRNA, smRNA, snRNA, or other small non-coding RNA. See, e.g., US Patent Applications 20050272923, 20050266552, 20050142581, and 20050075492. A "microRNA precursor" refers to a nucleic acid having a stem-loop structure with a microRNA sequence incorporated therein.

A "stem-loop structure" refers to a nucleic acid having a secondary structure that includes a region of nucleotides which are known or predicted to form a double strand (step portion) that is linked on one side by a region of predominantly single-stranded nucleotides (loop portion). The terms "hairpin" and "fold-back" structures are also used herein to refer to stem-loop structures. Such structures are well known in the art and these terms are used consistently with their known meanings in the art. The actual primary sequence of nucleotides within the stem-loop structure is not critical to the practice of the invention as long as the secondary structure is present. As is known in the art, the secondary structure does not require exact base-pairing. Thus, the stem may include one or more base mismatches. Alternatively, the base-pairing may be exact, i.e. not include any mismatches.

The term "partial complementarity" refers to at least a portion of the nucleic acid sequences that are capable of base pairing. For instance, in some embodiments two nucleic acid sequences that have partial complementarity have at least 10 nucleotides that are capable of base pairing. In some instances, at least 15 nucleotides in each sequence are capable of participating in a base pairing interaction with one another. In other instances, the two nucleic acids are perfectly complementary, and thus all nucleotides in each sequence are capable of base pairing with a corresponding nucleotide in the other nucleic acid sequence.

The term "region" refers to a portion of a nucleic acid having at least one identifiable sequence, structure, function, or characteristic. Within regions of target nucleic acids are segments. A "segments" refers to a smaller or sub-portion of a region within a nucleic acid.

A "coding region" refers to the region between the translation initiation codon and the translation termination codon, is also a region which may be targeted effectively. It can also refers to a region corresponding to an exon. A 5' untranslated region (5'UTR) refers to the portion of an mRNA in the 5' direction from the translation initiation codon, and thus including nucleotides between the 5' cap site and the translation initiation codon of an mRNA (or corresponding nucleotides on the gene). A 3' untranslated region (3'UTR) refers to the portion of an mRNA in the 3' direction from the translation termination codon, and thus including nucleotides between the translation termination codon and 3' end of mRNA (or corresponding nucleotides on the gene). The 5' cap site of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap site. It is also suitable to target the 5' cap region.

A "biological sample" refers to a sample obtained from a cell culture or a biological subject, including sample of biological tissue or fluid origin, obtained, reached, or collected in vivo or in situ, that contains or is suspected of containing nucleic acids or polypeptides of interest. A biological sample also includes samples from a region of a biological subject containing precancerous or cancer cells or tissues. Such samples can be, but are not limited to, organs, tissues, fractions and cells isolated from mammals including, humans such as a patient, mice, and rats. A biological sample also may include sections of tissues, for example, frozen sections taken for histologic purposes. A biological sample is typically of an eukaryotic origin, for example, insects, protozoa, birds, fish, reptiles, and preferably a mammal, for example, rat, mouse, cow, dog, guinea pig, or rabbit, and more preferably a primate, for example, a chimpanzee or a human.

The details of one or more embodiments of the invention are set forth in the accompanying drawings and the description below. Other features, objects, and advantages of the invention will be apparent from the description and drawings, and from the claims.

DETAILED DESCRIPTION

The invention relates to methods that employ bioinformatic techniques to construct a high-throughput computational pipeline. In particular, it relates to genome-wide, sequence-based computational methods for microRNA precursor identification. The microRNAs precursor-identifying methods of this invention are based on nucleotide sequences, secondary structures, and motif enrichment. Since they do not need a pre-established training set, profile, or pattern, the efficiency is fairly high. They are useful for identifying novel microRNAs and their targets.

It is known that a microRNA is transcribed as a precursor RNA that contains an RNA stem loop of approximately 80 nucleotides from which the mature single stranded molecule is excised. MicroRNAs can be subdivided into two groups based on their mechanism of gene regulation. The first class of miRNAs are complementary to their target sequences and direct RNA cleavage (i.e., via RNA interference or RNAi). Prediction of this class of microRNA is possible using sequence similarity searches (Rhoades et al., 2002, Cell, 110, 513~520). The second class of miRNAs, exemplified by *C. elgans* miRNAs lin-4 and let7, match their target sequences imperfectly and do not direct RNA cleavage. This imperfect binding has been shown to allow for bulges, mismatches and non-canonical G:U pairing in the middle of the mRNA target. The lin-4 and let7 miRNAs regulate translation of target mRNAs. Alignment of these microRNAs to their targets requires allowing for gaps of variable lengths at variable positions and sequence mismatches. This makes microRNA prediction a difficult computational task.

It is believed that hundreds of microRNAs exist in the human genome. Functions are known for hardly any of these, but they are likely to be involved in most, if not all, areas of cell regulation. The methods of this invention are useful for identifying novel microRNAs and their targets.

Molecular mechanisms by which microRNAs regulate gene expression are currently being clarified, but individual biological functions remain largely unknown. It is believe that temporal and spatial expression of microRNAs play key roles in driving cellular specificity. Methods of this invention can be used to define the spatial expression of microRNAs in animals. Novel miRNAs sequences and their target sequences obtainable by the methods are useful in gene regulation.

Figure 1:
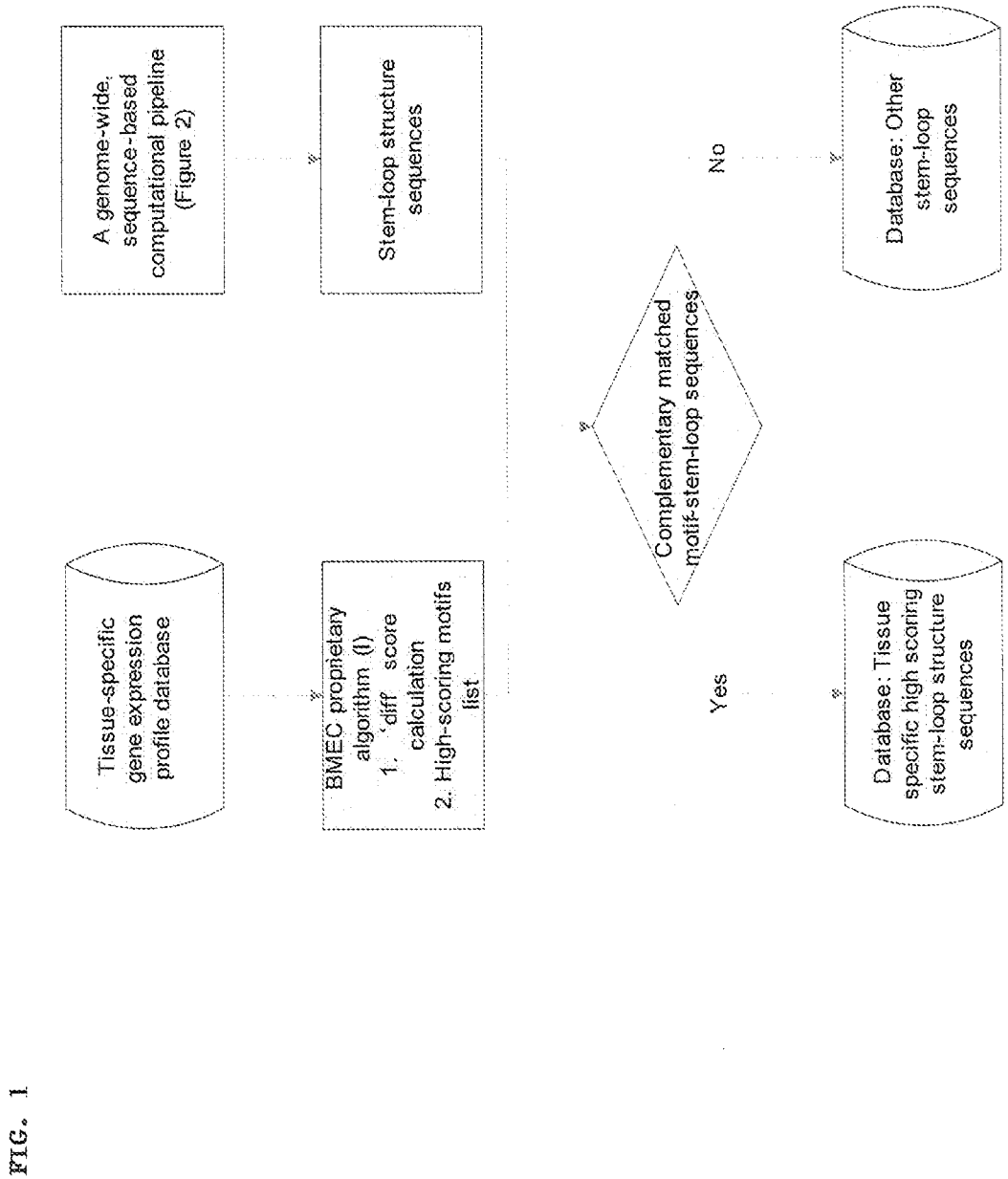
FIG. 1 is a flow chart of an algorithm for identifying microRNA precursors specific or non-specific to a tissue.

Shown in FIG. 1 is a flow chart of a main algorithm, on which a preferred embodiment of this invention is based. The algorithm includes two parts.

Part 1, shown on the upper left side, relates to a BMEC proprietary algorithm for identifying microRNA motifs from one or a set of target genes. It takes the advantage of a so-called 3' UTR-motif enrichment phenomenon in the target sequences of known microRNAs (Lim et al., 2005, Nature, 433, 769~773; and Xie et al., 2005 Nature, 434, 338~345). The BMEC algorithm (I)' scores motifs by the relationship between a motif and microRNAs rather than by the regularly conservation concept. In order to evaluate the 3' UTR enrichment of a motif within a target gene set, a value, named "DIFF" is used to represent the degree of 3' UTR enrichment of a motif. The higher the DIFF of a motif is, the stronger the relationship between the motif and microRNA is. The value "DIFF" is a function of two variables, "OBS" and "EXP." The "OBS" represents the observed count of a motif within a region, such as 5' UTR, CDS or 3'UTR, of a target gene set. The "EXP" represents the expected count of a motif estimated within a region of all gene transcripts. See Functions (I) and (II) above. A preferred embodiment of this invention is based on Formula III and IV shown above. After calculating the DIFF values of all test motifs in a target gene set, one can identify the motifs with higher DIFF values, which are more likely present in microRNA sequences.

These identified motifs can be compared to microRNAs precursors identified by Part II of the above-mentioned main algorithm to identify microRNA precursors that are specific or non-specific for a set of target genes.

Figure 2:
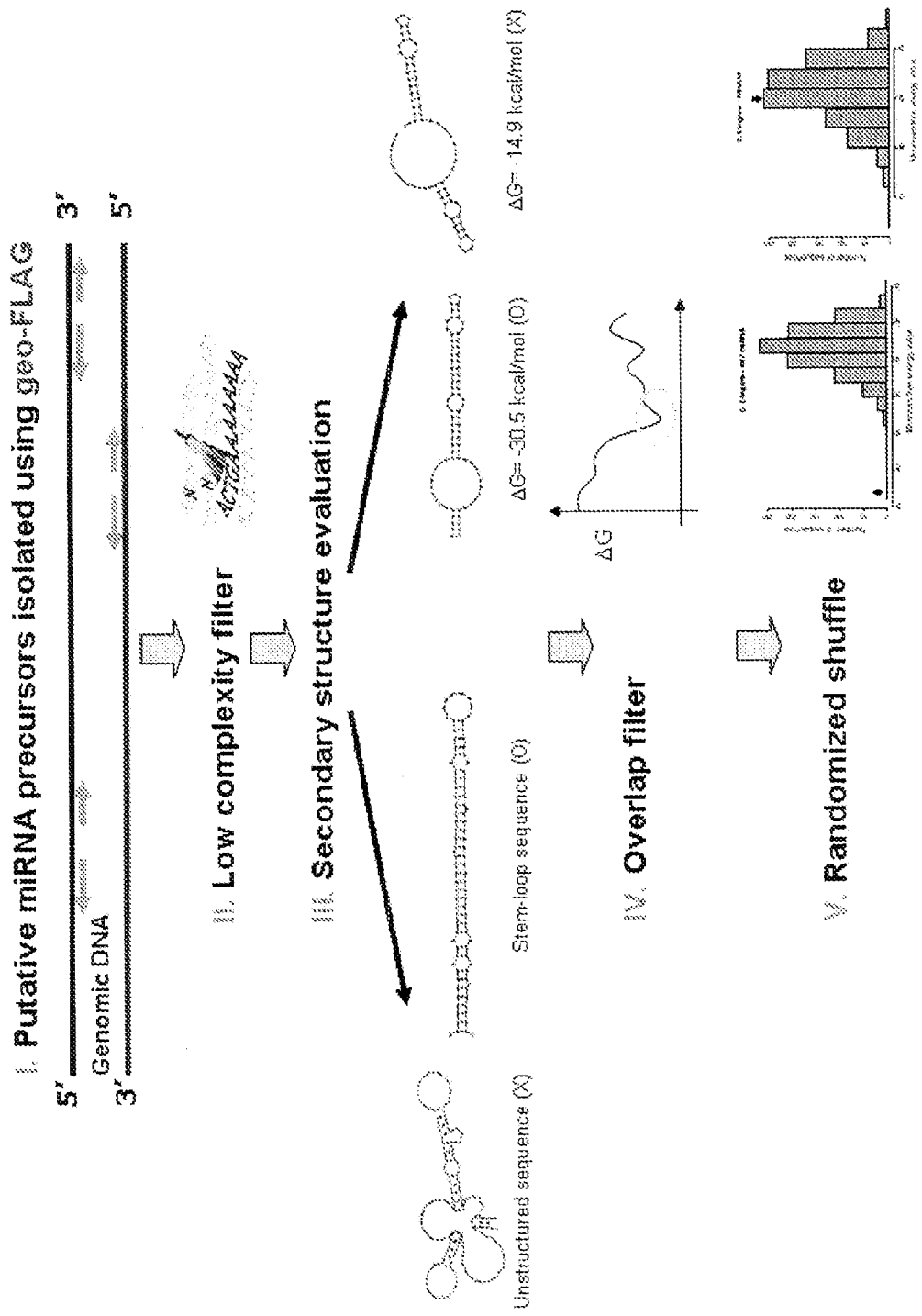
FIG. 2 is a diagram showing steps of a method for identifying microRNA precursors.

Part 2, shown on the upper right side, relates to a computation pipeline that analyzes DNA sequences on the basis of their sequence and structural properties. It allows one to quickly identify microRNAs precursors in a whole genome. This computational pipeline is composed of a cascade of stages or filters. Criterion with increasing stringency is applied as the computation proceeds to the next stage. The pipeline first looks for regions in genomic DNA sequences that have potential to form short hairpins. It then filters out regions that reside in the low complexity regions. Next it examines the thermodynamic properties and secondary structures of retained regions. The candidates are furthered screened according to their geometric shapes. Finally, it uses randomized test to search for the potential precursors with stable secondary structure. This pipeline can be divided into Stages I-V as shown in FIG. 2, which are elaborated on below.

(I) geo-FLAG

Based on the assumption that functionally important molecules tend to be conserved in sequence and structure across species, several groups have employed comparative genomics approach to detect potential microRNA precursors (Grad et al., 2003, Mol. Cell, 11, 1253-63; Berezikov et al., 2005, Cell, 120, 21-24; and Wang et al., 2005, Bioinformatics, 21, 3610-3614). Known microRNA precursors are collected and used as a training set. The entire genomic DNA sequence are scanned against this set using common sequence alignment tools such as BLAST (Altschul et al., 1997, Nucleic Acids Res., 23, 3389-3402). However, BLAST is not suitable for this task for the following reasons. First, the length (~70 nt) of a typical microRNA precursor is short. Therefore, it is necessary to use a word size much shorter than the default value 11 for BLASTN. Second, extension strategy must be changed to match complementary base pair (including G-T or G-U wobble pairings). Third, substantial efforts are required to post-process the BLAST results to identify possible sequence regions that may form a hairpin structure characteristic of microRNA precursors. Fourth, novel microRNA precursors may be missed simply because they do not "resemble" any known member in the training set.

To facilitate the identification of short hairpins in genomic DNA sequences, we modified a BMEC-proprietary algorithm, FLAG (Fast Local Alignment for Gigabase), a tool for rapid large-scale DNA sequence alignment. This variation of FLAG is called "geo-FLAG." The prefix "geo" stands for geometry, indicating that the FLAG kernel is specially designed for the identification of sequence regions that may form particular geometric shapes, such as a stem-loop or hairpin in our case. Like smaloop (Grad et al., 2003, Mol. Cell, 11, 1253-63) geo-FLAG adopts the seed-and-extension paradigm. It looks for short complementary words within a specified distance and uses a heuristic method to accelerate the extension. Compared to BLAST, geo-FLAG supports shorter word lengths and aligns complementary base pairs (including G-Us).

(II) Low Complexity Filter

Fragments obtained from the geo-FLAG stage are further filtered to remove those with low complexity. Repeat-masked genomic DNA sequences are downloaded from Ensembl website and compared with the original sequences. In this way, the low complexity regions are identified. All fragments that fall into these regions are discarded. This stage effectively removes more than 60 percent of the candidates.

(III) Secondary Structure Evaluation

The sequence fragments that pass the first two stages have potential to from short hairpins, since they comprise two imperfectly complementary segments within a short range. However, it is necessary to evaluate their thermodynamic properties and RNA secondary structures. For this purpose, Vienna RNA package can be used to examine the minimum free energies of folding and the geometric shapes of these fragments. Sequence fragments that do not form simple hairpins have inappropriate loop sizes or stem lengths, or have unfavorable minimum free energies are discarded.

(IV) Overlap Filter

It is common that geo-FLAG identifies two sequence fragments that overlap with each other significantly. To remove such redundant fragments, overlap filter is applied. Since many microRNA precursors are located in a microRNA cluster (Tanzer et al., 2004, J Mol Biol., 339, 327-335), care should be taken when merging the neighboring fragments so that the potential precursors would not be lost.

(V) Randomized Shuffle

It is known that, in contrast to transfer RNAs and ribosomal RNAs, the great majority of microRNA precursors exhibit a folding energy that is significantly lower than those for shuffled sequences. Accordingly, a randomized test is conducted to screen for the microRNA precursors with highly stable secondary structures. (Bonnet et al., 2004, Bioinformatics, 20, 2911-2917).

In the prediction of RNA secondary structures, contributions from neighboring bases are important to minimum free energy. To assess the stability of the secondary structure, an algorithm that randomly shuffles the sequence while preserving the mono-nucleotide and di-nucleotide frequencies (Workman et al., 1999, Nucleic Acids Res., 27, 4816-4822) can be employed to perform randomized shuffle 1,000 times for each microRNA precursor candidates. The probability p that shuffled sequences have lower energy of folding is calculated. Only those candidates with sequence composition that give rise to very small p (e.g. $\leq 0.005$) or stable secondary structure are retained.

The microRNA motifs and microRNAs precursors respectively identified by Parts 1 and 2 are compared identify microRNA precursors that are specific or non-specific for a target gene or a set of target genes. This step is referred as Stage (VI) and shown on the lower part of FIG. 1. A microRNAs precursor is determined to be specific for the set of target genes if it contains a segment that is identical or complementary to the microRNA motif. Otherwise, it is determined to be a non-specific microRNA precursor for the target gene or the set of target genes. The sequences of each groups of microRNAs precursors thus-identified can be stored on one or more computer readable media to generate databases.

The invention can be implemented in digital electronic circuitry, or in computer hardware, firmware, software, or in combinations thereof. Apparatus of the invention can be implemented in a computer program product tangibly embodied in a machine-readable storage device for execution by a programmable processor; and method actions can be performed by a programmable processor executing a program of instructions to perform functions of the invention by operating on input data and generating output. The invention can be implemented advantageously in one or more computer programs that are executable on a programmable system including at least one programmable processor coupled to receive data and instructions from, and to transmit data and instructions to, a data storage system, at least one input device, and at least one output device. Each computer program can be implemented in a high-level procedural or object oriented programming language, or in assembly or machine language if desired; and in any case, the language can be a compiled or interpreted language. Suitable processors include, by way of example, both general and special purpose microprocessors. Generally, a processor receives instructions and data from a read-only memory and/or a random access memory. A computer can include one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including, by way of example, semiconductor memory devices, such as EPROM, EEPROM, and flash memory devices; magnetic disks such as, internal hard disks and removable disks; magneto-optical disks; and CD_ROM disks. Any of the foregoing can be supplemented by, or incorporated in, ASICs (application-specific integrated circuits).

In addition, the present invention provides a system having a computer, one or more databases containing the cataloged microRNAs precursor or microRNA motif sequences, and a communication link connecting the computer to the one or more databases. The computer is used to select one or more tissue expression or genomic characteristics, select a target gene that is related to the selected characteristics, compare the genomic sequence of the selected gene sequence to the cataloged microRNAs precursor or microRNA motif sequences, extract any cataloged microRNAs precursor or microRNA motif sequences that contain a portion of or match to the genomic gene sequence, align the selected genomic sequence to each extracted microRNAs precursor or microRNA motif sequence, output the extracted sequence. In this system, data (e.g., genomic sequences, tissue-specific gene expression profiles, or cataloged microRNAs precursor or microRNA motif sequences) may be input by downloading from a local site such as a memory or a disk drive, or alternatively from a remote site over a network such as the Internet. The sequences may also be input by keyboard, if necessary.

The microRNAs precursors identified by methods of this invention can be used to regulate the expression of corresponding target genes and develop therapeutics. Depending on functions of a target gene, matching microRNAs precursors can be used treat disorders caused by or associated with abnormal higher level of the target gene. Techniques for making a microRNA-based therapeutic agent and delivering it to a subject in need thereof are known in the art. See, e.g., WO 2005/017111, WO 2004/066183, and US Patent Application 20050186589.

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

Example

The above-described method was used to identify microRNA precursors using the sequences of the plus strands of human chromosomes 19 and 22. MicroRNA reference sets and gene sequences were obtained from the following databases: miRBase v7.0 (http://microma.sanger.ac.uk/sequences/index.shtml), miRNA expression data from GEO (GSE2564) (http://www.ncbi.nlm.nih.gov/geo/query/acc.egi?acc=GSE2564), Ensembl Human genomic DNA database v33 (NCBI build 35.1) (ftp://ftp.ensembl.org/), NCBI RefSeq database (http://www.ncbi.nlm.nih.gov/RefSeq/), GNF SymAtlas v1.1.1 (http://symatlas.gnf.org/SymAtlas/).

In Part 1 of the main algorithm, the gene set of whole GNF brain database was processed to identify bran-specific micro RNA motifs. A serial of 6-mer motifs were selected. Motifs having both "$DIFF_{CDS}$" and "$DIFF_{5'UTR}$" of greater than 0 were retained. Some of these retained motifs are shown in Table 1 below. The "diff_sum" shown in Table 1 is the summary of $DIFF_{CDS}$ and $DIFF_{5'UTR}$. Remarkably, found in Table 1 is a motif (ccuuaa) that has a diff_sum value of 4.3302 and is related to a known brain microRNA, hsa-mir-124a.

To verify the reliability of the selected motifs (algorithm-selected motifs), a set of 6-mer motifs were randomly selected (randomly-selected motifs). The distribution of microRNAs matching the algorithm-selected motifs or randomly-selected motifs was plotted against the matching mature microRNAs' positions from 5' end to 3' end ("microRNA count vs. the microRNA mature position matching 6-mer motif").

It was found that algorithm-selected motifs match known microRNAs on their 5' side more than on the 3' side. In other words, the matching positions are more concentrated on the 5' side. In contrast, randomly-selected motifs match mature microRNAs more evenly along the microRNAs. These results are consistent with the result described in Xie et al., 2005, Nature, 434, 338~345, demonstrating that the algorithm-selected motifs are valid.

TABLE 1

| Motifs | Diff_sum | miRNew(Brain, GNF) |
|---|---|---|
| uuuuuu | 5.8886 | New |
| uuaauu | 5.6921 | New |
| uaggua | 5.6912 | New |
| uuuuua | 5.5475 | New |
| uaauuu | 5.6029 | New |
| guuuuu | 5.5834 | New |
| uauaua | 5.5729 | New |
| uguuuu | 5.5553 | New |
| uuuuaa | 5.5223 | hsa-miR-130a |
| uaugua | 5.5167 | New |
| uuguuu | 5.5005 | New |
| uuuugu | 5.4744 | hsa-miR-153 |
| uauuuu | 5.4718 | New |
| uuuguu | 5.4683 | New |
| uuuaau | 5.4231 | New |
| uuauuu | 5.4048 | New |
| uaaauu | 5.4046 | New |
| uuugua | 5.3919 | hsa-miR-193 |
| uaguuu | 5.3861 | New |
| uuaagu | 5.3860 | New |
| uuuaaa | 5.3796 | New |
| guauag | 5.3685 | New |
| guaaau | 5.3640 | New |
| uaauac | 5.3543 | New |
| uaguua | 5.3518 | New |
| uguaua | 5.3509 | New |
| uaaaau | 5.3495 | New |
| uuaguu | 5.3471 | New |
| auauau | 5.3330 | New |
| uuuuau | 5.3259 | New |
| cuuuuu | 5.2886 | New |
| uaaguu | 5.2766 | New |
| uuguau | 5.2756 | New |
| uguauu | 5.2706 | New |
| uaauua | 5.2586 | New |
| uuaaaa | 5.2530 | New |
| uauuau | 5.2488 | New |
| auuuuu | 5.2451 | New |
| uauuua | 5.2393 | hsa-miR-16 |
| uuuagu | 5.2372 | New |
| uuuuag | 5.2238 | New |
| uuuuuc | 5.2213 | New |
| auaguu | 5.2089 | New |
| uuaaau | 5.2075 | New |
| uuguaa | 5.2032 | New |
| uaguau | 5.2021 | New |
| auuucu | 4.4686 | hsa-miR-195 |
| gugugu | 4.4681 | New |
| cuugua | 4.4662 | New |
| uuuugc | 4.4621 | hsa-miR-19a, hsa-miR-19b |
| uagcau | 4.4616 | New |
| gauuuu | 4.4615 | New |
| uuguug | 4.4578 | New |
| uaacug | 4.4568 | New |
| guauug | 4.4552 | New |
| guaguu | 4.4549 | New |
| ucuguu | 4.4508 | New |
| uaaauc | 4.4491 | New |
| uuauac | 4.4469 | New |
| uugcau | 4.4450 | hsa-miR-19a, hsa-miR-19b |
| uuagcu | 4.4435 | New |
| cuuaac | 4.4420 | New |
| uucaua | 4.4420 | New |
| augugu | 4.4418 | New |
| cuguaa | 4.4413 | hsa-miR-106a, hsa-miR-17-5p |
| uuaaga | 4.4362 | New |
| acuaac | 4.4361 | New |
| uuuagc | 4.4354 | New |
| gcuuuu | 4.4333 | hsa-miR-320 |
| uuuuga | 4.4303 | New |
| uuacuu | 4.4218 | hsa-miR-26a, hsa-miR-26b_(sub_1) |
| uguaca | 4.4149 | hsa-let-7g, hsa-miR-103, hsa-miR-107 |
| uaucuu | 4.4148 | New |
| aauuug | 4.4140 | New |
| cuaggu | 4.4122 | New |
| ugcaua | 4.4106 | hsa-miR-19a |
| guaagc | 4.4098 | hsa-miR-106a, hsa-miR-17-5p |
| acugua | 4.4054 | hsa-let-7g, hsa-miR-101, hsa-miR-106a, hsa-miR-139, hsa-miR-17-5p |
| aauuau | 4.4053 | hsa-miR-126* |
| aaaugu | 4.4052 | New |
| auuaac | 4.3966 | New |
| aacuaa | 4.3958 | New |
| ugcuuu | 4.3937 | New |
| acuagu | 4.3892 | hsa-miR-224, hsa-miR-7 |
| cauuua | 4.3854 | New |
| aguuau | 4.3843 | hsa-miR-101 |
| guuaua | 4.3792 | New |
| ucuuau | 4.3787 | New |
| acuugu | 4.3787 | New |
| uacugu | 4.3781 | hsa-miR-101 |
| uauuuc | 4.3772 | hsa-miR-195 |
| aacuuu | 4.3686 | New |
| uguacu | 4.3660 | New |
| acuuua | 4.3636 | hsa-miR-20_(sub_1) |
| cuauau | 4.3630 | New |
| aguuua | 4.3629 | New |
| uaucua | 4.3621 | hsa-miR-9* |
| ugucuu | 4.3605 | New |
| auguua | 4.3555 | New |
| uguuau | 4.3526 | New |
| uuuccu | 4.3510 | New |
| acauau | 4.3502 | New |
| ucuagu | 4.3477 | New |
| ugcauu | 4.3441 | New |
| cuuagu | 4.3456 | New |
| cauaua | 4.3408 | New |
| cuuuau | 4.3398 | New |
| auaacu | 4.3383 | New |
| acuuag | 4.3366 | hsa-miR-27a, hsa-miR-27b |
| uugagu | 4.3315 | New |
| ccuuaa | 4.3304 | hsa-miR-124a |
| uaggcu | 4.3301 | New |
| usaaac | 4.3299 | hsa-miR-140 |
| cuaagu | 4.3288 | New |
| gucuua | 4.3251 | New |
| agugua | 4.3231 | hsa-miR-30b, hsa-miR-30c |
| caugua | 4.3229 | New |
| auguag | 4.3226 | hsa-miR-221 |
| auauug | 4.3205 | New |

TABLE 1-continued

| Motifs | Diff_sum | miRNew(Brain, GNF) |
|---|---|---|
| uacauu | 4.3171 | hsa-miR-1 |
| acuauu | 4.3170 | hsa-miR-301 |
| ugcuua | 4.3170 | New |
| uagaaa | 4.3162 | New |
| uuggua | 4.3147 | New |
| acuaaa | 4.3109 | New |
| aaauag | 4.3105 | New |
| uaauuc | 4.3085 | New |
| ucuaua | 4.3079 | New |
| ucuaua | 4.3072 | New |
| uuccuu | 4.3070 | New |
| uugaua | 4.3054 | New |
| auaggg | 4.3029 | hsa-miR-140 |
| cauuaa | 4.3023 | New |
| uuaucu | 4.3023 | hsa-miR-9* |
| uguuuc | 4.3002 | New |
| uuuaca | 4.2999 | hsa-miR-1, hsa-miR-30a*, hsa-miR-30b, hsa-miR-30c, hsa-miR-30d, hsa-miR- |

TABLE 2

| | | Chromosome | | | | | |
| | | 19 (+), 63.8 MB | | | 22 (+), 49.5 MB | | |
| Step | | Criteria | Candidate number | Percentage | Found/Known | Candidate number | Percentage | Found/Known |
|---|---|---|---|---|---|---|---|---|
| I | geo-FLAG | Hairpin | 705,509 | 100.00% | 5/5 | 437,627 | 100.00% | 3/3 |
| II | Low complexity | non-repeat sequences | 278,160 | 39.43% | 5/5 | 196,269 | 44.85% | 3/3 |
| III | Secondary structure evaluation | 1. loop <20 and stem >20<br>2. $\Delta G \leq -25$ kcal/mol | 39,590 | 5.60% | 4/5 | 20,828 | 4.76% | 3/3 |
| IV | Overlap | Minimum free energy candidate | 38,980 | 5.53% | 4/5 | 20,712 | 4.73% | 3/3 |
| V | Randomized shuffle | $p \leq 0.005$ | 6,330 | 0.90% | 4/5 | 3,616 | 0.83% | 3/3 |
| VI | motif | High Scoring 6-mers list | 4,811 | 0.68% | 4/5 | 2,722 | 0.62% | 3/3 |

As shown in Table 2, the pipeline (stages I-V) eliminated more than 99 percent of candidates and identified 4811 candidate microRNA precursors from the initial pool of 705,509 candidates, while 4 out 5 known microRNA precursors were retained ("Found/Known") for human chromosome 19, demonstrating a high sensitivity and a high specificity. These results suggest the presence of significantly higher numbers of miRNAs in the human genome than previously estimated.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A computer system for identifying a microRNA motif for a set of one or more target genes, comprising:
   one or more processors configured to execute program instructions; and
   a computer-readable medium containing executable instructions that, when executed by the one or more processors, cause the computer system to perform a method for identifying a microRNA motif for a set of one or more target genes, the method comprising:
   (a) providing a set of subject nucleic acid sequences that contain coding regions (CDRs), 5' untranslated regions (5' UTRs), and 3' untranslated regions (3' UTRs) of the set of one or more target genes;
   (b) selecting at least one test RNA motif from the subject nucleic acid sequences;
   (c) determining the $DIFF_{CDRs}$ or $DIFF_{5'UTRs}$ value of the at least one test RNA motif in the subject nucleic acid sequences by a set of functions as follows:

$$DIFF_{CDRs} = f(OBS_{3'UTRs}, OBS_{CDRs}, EXP_{3'UTRs}, EXP_{CDRs}) \quad (I)$$

$$DIFF_{5'UTRs} = g(OBS_{3'UTRs}, OBS_{5'UTRs}, EXP_{3'UTRs}, EXP_{5'UTRs}) \quad (II)$$

in which
   $DIFF_{CDRs}$ and $DIFF_{5'UTRs}$ represent the degrees of the enrichment of the at least one test RNA motif in all of the 3' untranslated regions in comparison with all of the coding regions and all of the 5' untranslated regions, respectively;
   $OBS_{3'UTRs}$, $OBS_{CDRs}$, and $OBS_{5'UTRs}$ represent the observed counts of the at least one test RNA motif within all of the 3' untranslated regions, all of the coding regions, and all of the 5' untranslated regions, respectively, of the set of one or more target genes;
   $EXP_{3'UTRs}$, $EXP_{CDRs}$, and $EXP_{5'UTRs}$ represent the expected counts of the at least one test RNA motif within all of the 3' untranslated regions, all of the coding regions, and all of the 5' untranslated regions, respectively, of all gene transcripts; and
   wherein the set of functions take the form of Formula III and IV below:

$$DIFF_{CDRs} = \frac{OBS_{3'UTRs} - OBS_{CDRs}}{MAX(EXP_{3'UTRs}, EXP_{CDRs})} \text{ and} \quad (III)$$

$$DIFF_{5'UTRs} = \frac{OBS_{3'UTRs} - OBS_{5'UTRs}}{MAX(EXP_{3'UTRs}, EXP_{5'UTRs})}; \quad (IV)$$

and
   (d) selecting the at least one test RNA motif having both $DIFF_{CDRs}$ and $DIFF_{5'UTRs}$ greater than 0 as a microRNA motif.

2. The method of claim 1, wherein the test RNA motif is a contiguous segment containing 5 to 11 nucleotides.

3. The method of claim 1, wherein the set of target genes are expressed in a pre-determined biologic sample.

4. The method of claim 3, wherein the biologic sample is obtained from a tissue.

5. The method of claim 3, wherein the biologic sample is obtained from a cell culture.

6. The method of claim 3, wherein the set of target genes is determined from the microarray expression profiles provided by the Genomics Institute of the Novartis Research Foundation.

7. The method of claim 4, wherein the tissue is a brain tissue.

8. The method of claim 4, wherein the tissue is a liver tissue.

9. The method of claim 5, wherein the cell culture is a HepG2 cell culture.

10. A computer-implemented method for identifying a microRNA motif for a set of one or more target genes, the method comprising
(a) providing a set of subject nucleic acid sequences that contain coding regions (CDRs), 5' untranslated regions (5' UTRs), and 3' untranslated regions (3' UTRs) of the set of one or more target genes;
(b) selecting at least one RNA motif from the subject nucleic acid sequences;
(c) determining, at the computer, the $DIFF_{CDRs}$ or $DIFF_{5'UTRs}$ value of the at least one test RNA motif in the subject nucleic acid sequences by a set of functions as follows:

$$DIFF_{CDRs} = f(OBS_{3'UTRs}, OBS_{CDRs}, EXP_{3'UTRs}, EXP_{CDRs}) \quad (V)$$

$$DIFF_{5'UTRs} = g(OBS_{3'UTRs}, OBS_{5'UTRs}, EXP_{3'UTRs}, EXP_{5'UTRs}) \quad (VI)$$

in which
$DIFF_{CDRs}$ and $DIFF_{5'UTRs}$ represent the degrees of enrichment of the at least one test RNA motif in all of the 3' untranslated regions in comparison with all of the coding regions and all of the 5' untranslated regions, respectively;
$OBS_{3'UTRs}$, $OBS_{CDRs}$, and $OBS_{5'UTRs}$ represent the observed counts of the at least one test RNA motif within all of the 3' untranslated regions, all of the coding regions, and all of the 5' untranslated regions, respectively, of the set of one or more target genes;
$EXP_{3'UTRs}$, $EXP_{CDRs}$, and $EXP_{5'UTRs}$ represent the expected counts of the test RNA motif within all of the 3' untranslated regions, all of the coding regions, and all of the 5' untranslated regions, respectively, of all gene transcripts; and
wherein the set of functions take the form of Formula VII and VIII below:

$$DIFF_{CDRs} = \frac{OBS_{3'UTRs} - OBS_{CDRs}}{MAX(EXP_{3'UTRs}, EXP_{CDRs})} \text{ and} \quad (VII)$$

$$DIFF_{5'UTRs} = \frac{OBS_{3'UTRs} - OBS_{5'UTRs}}{MAX(EXP_{3'UTRs}, EXP_{5'UTRs})}; \quad (VIII)$$

and
(d) selecting the at least one test RNA motif having both $DIFF_{CDRs}$ and $DIFF_{5'UTRs}$ greater than 0 as a micro RNA motif.

11. The method of claim 10, wherein the test motif is a contiguous segment containing 5 to 11 nucleotides.

12. A computer program product, comprising a tangible computer readable medium comprising executable instructions for effecting the following steps:
receiving a set of subject nucleic acid sequences;
selecting at least one RNA motif from the subject nucleic acid sequences;
determining a $DIFF_{CDRs}$ or $DIFF_{5'UTRs}$ value for the at least one RNA motif in the subject nucleic acid sequences by a set of functions as follows:

$$DIFF_{CDRs} = f(OBS_{3'UTRs}, OBS_{CDRs}, EXP_{3'UTRs}, EXP_{CDRs}) \quad (I)$$

$$DIFF_{5'UTRs} = g(OBS_{3'UTRs}, OBS_{5'UTRs}, EXP_{3'UTRs}, EXP_{5'UTRs}) \quad (II)$$

in which
$DIFF_{CDRs}$ and $DIFF_{5'UTRs}$ represent the degrees of enrichment of the test RNA motif in all of the 3' untranslated regions in comparison with all of the coding regions and all of the 5' untranslated regions, respectively;
$OBS_{3'UTRs}$ and $OBS_{CDRs}$ represent the observed counts of the at least onetest RNA motif within all of the 3' untranslated regions, all of the coding regions, and all of the 5' untranslated regions, respectively, of the subject nucleic acid sequences;
$EXP_{3'UTRs}$, $EXP_{CDRs}$, and $EXP_{5'UTRs}$ represent the expected counts of the at least one test RNA motif within all of the 3' untranslated regions, all of the coding regions, and all of the 5' untranslated regions, respectively, of all gene transcripts; and
wherein the set of functions take the form of Formula III and IV below:

$$DIFF_{CDRs} = \frac{OBS_{3'UTRs} - OBS_{CDRs}}{MAX(EXP_{3'UTRs}, EXP_{CDRs})} \text{ and} \quad (III)$$

$$DIFF_{5'UTRs} = \frac{OBS_{3'UTRs} - OBS_{5'UTRs}}{MAX(EXP_{3'UTRs}, EXP_{5'UTRs})}; \quad (IV)$$

outputting the $DIFF_{CDRs}$ or $DIFF_{5'UTRs}$ value.

* * * * *

UNITED STATES PATENT AND TRADEMARK OFFICE
CERTIFICATE OF CORRECTION

| | | |
|---|---|---|
| PATENT NO. | : 7,941,278 B2 | |
| APPLICATION NO. | : 11/617038 | |
| DATED | : May 10, 2011 | |
| INVENTOR(S) | : Yu-Ching Chang et al. | |

It is certified that error appears in the above-identified patent and that said Letters Patent is hereby corrected as shown below:

In claim 1, column 14, line 52, "Formula" should read --Formulas--.

In claim 6, column 15, line 7, "set of target genes is" should read --set of target genes are--.

In claim 10, column 15, line 53, "Formula" should read --Formulas--.

In claim 10, column 16, line 10, "$DIFF_{CDRs}$, and" should read --$DIFF_{CDRs}$ and--.

In claim 10, column 16, lines 10-11, delete the line break between "micro" and "RNA" (should read --microRNA--).

In claim 12, column 16, line 15, "computer readable" should read --computer-readable--.

In claim 12, column 16, line 33, "$OBS_{3'UTRs}$ and $OBS_{CDRs}$" should read --$OBS_{3'UTRs}$, $OBS_{CDRs}$, and $OBS_{5'UTRs}$--.

In claim 12, column 16, line 34, "onetest" should read --one test--.

In claim 12, column 16, line 43, "Formula" should read --Formulas--.

Signed and Sealed this
Thirtieth Day of August, 2011

David J. Kappos
*Director of the United States Patent and Trademark Office*